United States Patent [19]

Erickson et al.

[11] 4,438,029
[45] Mar. 20, 1984

[54] SYNTHETIC PEPTIDES

[75] Inventors: Bruce W. Erickson, Closter, N.J.; Tony E. Hugli, San Diego, Calif.

[73] Assignee: Research Corporation, New York, N.Y.

[21] Appl. No.: 13,176

[22] Filed: Feb. 21, 1979

Related U.S. Application Data

[63] Continuation of Ser. No. 870,713, Jan. 19, 1978, abandoned, which is a continuation-in-part of Ser. No. 762,427, Jan. 25, 1977.

[51] Int. Cl.$^3$ .......................................... C07C 103/52
[52] U.S. Cl. ............................................. 260/112.5 R
[58] Field of Search ................................ 260/112.5 R

[56] References Cited

U.S. PATENT DOCUMENTS

| | | | |
|---|---|---|---|
| 3,216,993 | 11/1965 | Bodanezky et al. | 260/112.5 R |
| 3,230,211 | 1/1966 | Nicoloides | 260/112.5 R |
| 3,826,793 | 7/1974 | Blonbock et al. | 260/112.5 R |
| 3,850,904 | 11/1974 | Greven | 260/112.5 R |
| 3,966,701 | 6/1976 | Dorman et al. | 260/112.5 R |

FOREIGN PATENT DOCUMENTS

| | | | |
|---|---|---|---|
| 4313203 | 4/1964 | Japan | 260/112.5 R |
| 1488987 | 11/1975 | United Kingdom | 260/112.5 R |

OTHER PUBLICATIONS

Yonezawa et al., "Solid Phase Synthesis of a Peptide with the Sequence of Clupeine Z. 191–196, (1973).
J. A. Keverling, "Biological Activity and Chemical Structure", 1977, 107–112.

*Primary Examiner*—Delbert R. Phillips
*Attorney, Agent, or Firm*—Scully, Scott, Murphy & Presser

[57] ABSTRACT

Peptides containing at least four amino acid residues characterized by the presence of an amidino substituted α-amino acid such as arginine at the carboxyl terminus manifest activity to control smooth muscle contraction, histamine release and vascular permeability.

17 Claims, No Drawings

SYNTHETIC PEPTIDES

RELATED APPLICATIONS

This is a continuation of application Ser. No. 870,713 filed Jan. 19, 1978 abandoned which is in turn a continuation-in-part application Ser. No. 762,427 filed Jan. 25, 1977.

This invention is concerned with therapeutically useful peptides, their derivatives, and acid and basic salts of said peptides and derivatives.

The therapeutically useful peptides within the scope of this invention contain at least four amino acid moieties and may contain twelve, thirteen or even more such moieties.

The products of the invention are useful therapeutic agents because of their ability to contract smooth muscle, release histamine from mast cells and enhance vacular permeability. Certain compounds of the invention, as will be explained, are useful because they have the opposite effect. More specifically, some peptides within the scope of the invention are agonists or promoters, others are antagonists or inhibitors. Certain of them are useful for the treatment of cardiac arrhythmia.

The carboxyl terminus of the peptide is an amidino substituted α-amino acid such as arginine or canavanine. For convenience in description, it will be hereinafter referred to as arginine. The arginine is joined in a peptide bond through its α-amino group to the carboxyl group of a lower aliphatic carbon atoms, suitably containing up to four amino acids. The presently preferred second amino acids are glycine and alanine.

The third amino acid in the peptide is joined through its carboxyl group to the amino group of the second amino acid. It is a hydrophobic amino acid, such as isoleucine, leucine, valine, methionine, phenylalanine, tyrosine or tryptophan. Leucine is presently preferred because it is readily available in both D- and L-forms, and contributes satisfactorily to the activity of the peptide.

The identity of the fourth amino acid does not appear to be critical, although, to obtain useful activity, there should be a fourth amino acid. Substantially any of the twenty commonly occurring amino acids appear to be useful. Compounds with the highest order of activity are those in which the fourth amino acid is glycine or glutamine. However, other amino acids, such as alanine, asparagine, serine, tyrosine or phenylalanine, may also be conveniently employed.

The presence of a fifth hydrophobic amino acid which is hydrophobic, such as leucine, markedly increases the activity of the peptide. Other hydrophobic amino acids, such as those mentioned above, are also useful.

It has been observed that activity increases with increasing length of the peptide chain up to as high as thirteen amino acids. However, the expense of preparing polypeptides with appreciably more amino acid moieties does not presently appear to be justified by the modest improvements realized.

Those compounds within the scope of this invention in which the first amino acid is arginine are agonists. If the arginine is joined through its carboxyl group to the amino group of a lower aliphatic amino acid, such as glycine, proline, alanine or serine, the resulting products are antagonists. They will, at low dosage levels, inhibit the contraction of smooth muscle, the release of histamine and vacular permeability. The amino acid to which the arginine is joined could be termed an inhibitor amino acid. The presently preferred inhibitor amino acid is glycine because it is readily available, and can be added to the molecule without introducing a new asymmetric center.

It is also possible to modify the activity of the peptides of the invention in other ways, for example, utilizing a D-amino acid as a constituent of the peptide instead of the naturally occurring L-amino acids. Several products in which L-arginine is replaced with D-arginine resist the hydrolytic activity of carboxypeptidase-B. The product, therefore, is stable for an extended period of time, and can be used to prepare long acting dosage forms. The same result may also be achieved by substitution of proline in the second position.

Because of their amphoteric nature, the products of this invention can be utilized in the form of pharmaceutically acceptable salts which may be either metallic salts or acid addition satls. These salts have the advantage of water solubility and are particularly useful for parenteral administration. The metallic salts, especially the alkali metal salts, are relatively stable and, for that reason, are often preferred over acid addition salts. The sodium salts are especially preferred because of their ease of preparation.

The acids which may be used to prepare the acid addition salts of this invention are those containing non-toxic anions and include, for example, hydrochloric, sulfuric, phosphoric, acetic, lactic, citric, tartaric, oxalic, succinic, maleic, gluconic, saccharic and like acids. In all, a wide variety of non-toxic derivatives of the polypeptides of this invention can be usefully employed. For example, the products, particularly those inhibitors with a glycine carboxyl terminus, can be reacted with thionyl chloride to form the acid chloride, and the latter reacted with ammonia to form an amide. Amines will, of course, form N-substituted amides.

Other useful derivatives may be obtained by modifying free functional groups on the peptide backbone. For example, free hydroxyl groups and free amino groups are readily derivatized. One very convenient class of derivatives is the class in which a free hydroxyl, which may be either aliphatic or aromatic, is esterified with an alkanoyl or alkenoyl group containing up to eighteen or more carbon atoms. Alternatively, a free amino group can be acylated with alkanoyl or alkenoyl groups containing up to about eighteen carbon atoms. In both instances, the preferred derivatives are those in which the derivatizing groups contain from eleven to eighteen carbon atoms because the longer hydrocarbon chains impart increased lipid solubility to the molecules and enhance their transport across cell barriers.

The products of this invention may be synthesized by any of a wide variety of techniques now available for the synthesis of simple and complex polypeptides and even relatively low molecular weight proteins. In general, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one acid and the carboxyl group of the other. The blocking groups should be selected for easy removal without adversely affecting the polypeptide, either by racemization or by hydrolysis of formed peptide bonds.

Certain amino acids have additional functional groups, for example, the hydroxyl group of tyrosine or of threonine. It is usually necessary to block these additional groups with an easily removed blocking agent, so that it does not interfere with the desired condensation for the formation of peptide bonds.

A large number of procedures have been devised by the art for the synthesis of polypeptides and a wide variety of blocking agents have been devised. Most of these procedures are applicable to the class of polypeptides to which this invention pertains. No useful purpose would be served by describing the application of all of them. Convenient procedures are listed in the examples.

The presently preferred procedure for the synthesis of the products of this invention is the Merrifield technique. In this procedure, an amino acid is bound to a resin particle as an ester bond, and the peptide is generated in a stepwise manner by successive additions of protected amino acids to the growing chain. The procedure is well known and has been described in many published articles; see, for example, Erickson, B. W. and Merrifield, R. B. (1976) Solid-Phase Peptide Synthesis in "The Proteins", Neurath and Hill, Academic Press, New York, pp. 255–527.

For convenience in describing this invention, the conventional abbreviations for the various amino acids will be used. They are all familiar to those skilled in the art but, for clarity, some of the important amino acids with which this invention is concerned are listed below:

Arginine—Arg
Alanine—Ala
Leucine—Leu
Glycine—Gly
Histidine—His
Serine—Ser
Glutamine—Gln As indicated above, the agonists of this invention enhance the contraction of smooth muscle, enhance the release of histamine, and increase vacular permeability. They are therapeutically useful to induce the inflammatory response in mammals who are deficient in this regard. Thus, they may be used to assist the body in generating its defense mechanism against invasion by infectious microorganisms or other stress. Antagonists are useful clinically in local or systemic episodic or traumatic smooth muscle contraction, histamine release or increased vascular permeability. They may be used, for example, in nasal aerosols during episodes of asthma or bronchial allergy. They may be employed as prophylactics for such syndromes as shock accompanying Dengue fever.

The products of this invention are useful mammalian therapeutic agents, and are effective for their stimulating and inhibiting activity at extremely low levels. The physician or veterinarian will determine the dosage which will be most suitable for a particular application. It may vary from patient to patient, depending upon the size of the patient, the condition under treatment, and other factors which are readily evaluated by those skilled in the art. The products may be administered at very high levels, even up to two or more grams per day. Normally, they will be provided in dosage units containing up to about 250 mg of the active ingredient. The number of units administered per day can be varied by prescription, depending upon the condition under treatment.

The products may be utilized alone, but will generally be administered with pharmaceutically acceptable non-toxic carriers, the proportions of which are determined by the suitability and the chemical nature of the particular carrier, the chosen route of administration, and standard pharmaceutical practice. For intravenous and intramuscular administration, they may be used in the form of a sterile solution containing other solutes, for example, enough saline or glucose to make the solution isotonic. For topical administration, they may be combined with suitable carriers, such as petrolatum or other inert semi-viscous materials. Enterically coated dosage units may be utilized in the form of tablets or capsules containing such excipients as starch, milk sugar, certain types of clay, etc.

While arginine is the presently preferred first amino acid, other α-amino acids such as canavanine are also useful. All may be considered as arginine analogs because of the presence of the omega amidino group [—C(=NH)—NH$_2$]. They may have a greater or lesser number of methylene or imino groups in the side chain attached to the α-carbon atom. In fact, one or more of these groups can be replaced by another group such as oxy, thio, imino or carbonyl. One or more hydrogens attached to carbon or nitrogen may be replaced with an alkyl group, typically containing up to six carbon atoms, but preferably methyl or ethyl. As indicated above, the acid may be in the D- or L-form.

The following non-limiting examples are given by way of illustration only.

EXAMPLE 1

Synthesis of
L-Alanyl-L-seryl-L-histidyl-L-leucyl-glycyl-L-leucyl-L-alanyl-L-arginine Preparation of Nα-tert-Butyloxycarbonyl-N$^g$-(4-toluenesulfonyl)-L-arginyl-oxymethyl-(styrene-copoly-1% divinylbenzene) (II). A solution of Nα-tert-butyloxycarbonyl-N$^g$-(4-toluenesulfonyl)-L-arginine (1.3 g) in ethanol (15 ml) and water (1.35 ml) was adjusted to pH 7.1 by addition of a solution of cesium bicarbonate (0.43 g) in water (1.35 ml). The resulting solution was evaporated to dryness at 40° C. under reduced pressure. Benzene (25 ml) was added and the mixture was evaporated to dryness under the same conditions; this process was repeated four more times. The resulting solid was dried for 2.5 hours at a pressure of 1 torr to give the cesium salt of Boc-Arg(Tos) (I) as a white solid (1.7 g). Chloromethyl-(styrene-copoly-1% divinylbenzene) (3.5 g; 0.23 mmol Cl per gram of polystyrene) was swelled in N,N-dimethylformamide (DMF; 15 ml) and mixed with a solution of the salt I (1.7 g) in DMF (10 ml). The mixture was mechanically stirred and maintained at 50° C. for 75 hours. A solution of the salt I (3.7 g) in DMF (25 ml) was added and the mixture was stirred and kept at 50° C. for 95 hours. The resin was collected on a sintered glass funnel and washed successively with DMF (three 25-ml portions), absolute ethanol (three 25-ml portions), and dichloromethane (three 25-ml portions). After being dried for 2 hours at 1 torr, the resin II (3.3 g) contained 0.17 mmol of arginine per gram of polystyrene as judged by treatment of 10-mg portions with 10% anisole in liquid HF for 30 minutes at 0° C., hydrolysis of the acid-soluble material with 6 N HCl for 24 hours at 110° C., and amino acid analysis of the hydrolysate.

Preparation of $N^\alpha$-tert-Butyloxycarbonyl-L-alanylh-$O^\beta$-benzyl-L-seryl-$N^{im}$-(4-toluenesulfonyl)-L-histidyl-L-leucyl-glycyl-L-leucyl-L-alanyl-$N^g$-(4-toluenesulfonyl)-L-arginyloxymethyl-(styrene-copoly-1% divinylbenzene) (III). The Boc-Arg(Tos)-resin II (2.0 g; 0.34 mmol arginine) was swelled in dichloromethane (40 ml) in a 75-ml glass reaction vessel bearing a sintered glass disk. By application of air or nitrogen pressure to the vessel and/or reduced pressure to the outlet below the sintered disk, the resin was filtered until most of the solution was removed.

A. The deprotection step was done by adding a solution of 1:1 (v/v) trifluoroacetic acid—dichloromethane (40 ml) to the vessel, stirring the mixture for 1 minute, and filtering as before. Then a second portion of the 1:1 (v/v) trifluoroacetic acid—dichloromethane (40 ml) was added, and the mixture was mixed for 30 minutes and filtered.

B. The washout step was accomplished in a similar manner by washing the resin successively with dichloromethane (five 40-ml portions for 1 minute each), with 2-propanol (two 40-ml portions for 1 minute each), and with dichloromethane (five 40-ml portions for 1 minute each).

C. The neutralization step was performed by washing the resin with 1:19 (v/v) ethyldiisopropylamine—dichloromethane (three 40-ml portions for 2 minutes each).

D. The washout step B was repeated.

E. The coupling step was carried out by adding to the resin a dichloromethane solution (10 ml) of the desired Boc-amino acid (3 mmol per mmol of initial arginine), mixing for 2 minutes, adding to the mixture a dichloromethane solution (10 mol) of N,N'-dicyclohexylcarbodiimide (3 mmol per mmol of initial arginine), mixing for 30 minutes, and filtering.

F. The washout step B was repeated.

G. The neutralization step C was repeated.

H. The washout step B was repeated.

I. The coupling step E was repeated.

J. The washout step B was repeated.

The execution of steps A through J constituted one cycle of the synthesis, during which one protected amino acid residue was added to the peptide. This cycle was conducted initially with Boc-L-alanine and successively with Boc-L-leucine, Boc-glycine, Boc-L-leucine, Boc-$N^{im}$-(4-toluenesulfonyl)-L-histidine, Boc-$O^\beta$-benzyl-L-serine, and Boc-L-alanine, where "Boc" denotes "$N^\alpha$-tert-butyloxycarbonyl."

Deprotection and Purification of L-Alanyl-L-seryl-L-histidyl-L-leucyl-glycyl-L-leucyl-L-alanyl-L-arginine (IV). Part of the protected octapeptide-resin III (0.26 g) was treated with 10% anisole in liquid HF (6 ml) for 1.0 hour at 0° C. After evaporation of the HF with a water aspirator and then vacuum pump, the resin was washed with ether (three 2-ml portions) to remove anisole and with trifluoroacetic acid (five 2-ml portions) to remove the peptide IV. After evaporation of the trifluoroacetic acid, the residue was dissolved in 5% aqueous acetic acid and lyophilized to afford the peptide, which was dissolved in 1% aqueous acetic acid (2 ml) and gel filtered on a 2.5 × 100-cm column of Bio-Gel P-2 (100–200 mesh, Bio-Rad) pumped with 1% acetic acid at 23 ml per hour. The major ninhydrin-positive peak (175 to 300 ml) was pooled and lyophilized. Part of the residue (19 mg) was dissolved in 0.01 M NaCl, 0.01 M NaH$_2$PO$_4$ (pH 4.5; 1.5 ml) and applied to a 1 × 50-cm column of carboxymethyl-cellulose (Cellex CM, Bio-Rad), which was pumped at 30 ml per hour with a linear salt gradient from 0.01 to 0.20 M NaCl (both solutions 100 ml, 0.01 M NaH$_2$PO$_4$, pH 4.5). The major peptide peak (130 to 170 ml) as judged by ultraviolet absorbance at 206 nm was pooled and lyophilized. The residual mixture of salt and peptide was dissolved in 1% acetic acid (2 ml) and desalted on a 1.5 × 85-cm column of Bio-Gel P-2 pumped with 1% acetic acid at 15 ml per hour. The major peptide peak (50 to 75 ml) as judged by absorbance at 206 nm was pooled and lyophilized to provide the pure octapeptide IV (10 mg). This material gave the expected amino acid analysis (see Table I) and amino acid sequence as determined by automated Edman degradation. It also showed a single ninhydrin-positive and Pauly-positive spot by thin-layer chromatography (R$_f$ 0.73 versus valine at R$_f$ 0.64) in 15:12:10:3 (by volume) 1-butanol—water—pyridine—acetic acid and by high-voltage electrophoresis (R$_{Arg}$ 0.76 at pH 5.0 and R$_{Arg}$ 0.58 at pH 6.4, where R$_{Arg}$ is the distance between the centers of the peptide IV and valine spots divided by the distance between the centers of the arginine and valine spots).

Each of the other peptides listed in Tables I or II were prepared in essentially the same manner.

TABLE I

| No. | Amino Acid Sequence | Amino Acid Composition (Molar Ratios) | | | | | | | Tlc[a] (R$_f$) | Activity[b] (nmol) |
|---|---|---|---|---|---|---|---|---|---|---|
| | | His | Arg | Ser | Glu | Gly | Ala | Leu | | |
| 1. | Gly-Leu-Ala-Arg | 0 | 1.04 | 0 | 0 | 1.08 | 10.9 | 1.00 | 0.73 | 1200–1400 |
| 2. | Leu-Gly-Leu-Ala-Arg | 0 | 0.87 | 0 | 0 | 1.12 | 1.12 | 2.00 | 0.80 | 150–300 |
| 3. | His-Leu-Gly-Leu-Ala-Arg | 0.98 | 0.97 | 0 | 0 | 1.18 | 1.09 | 1.00 | 0.79 | 10–20 |
| 4. | Ser-His-Leu-Gly-Leu-Ala-Arg | 0.99 | 1.00 | 0.93 | 0 | 1.06 | 1.05 | 2.00 | 0.77 | 6–10 |
| 5. | Ala-Ser-His-Leu-Gly-Leu-Ala-Arg | 0.95 | 1.00 | 0.97 | 0 | 1.13 | 1.94 | 1.94 | 0.73 | 5–8 |
| 6. | CH$_3$CO—Ala-Ser-His-Leu-Gly-Leu-Ala-Arg | 0.90 | 1.00 | 0.98 | 0 | 1.32 | 2.00 | 2.33 | 0.81 | 8–12 |
| 7. | Arg-Gln-His-Ala-Arg-Ala-Ser-His-Leu-Gly-Leu-Ala-Arg | 1.97 | 3.00 | 1.04 | 1.10 | 1.11 | 3.30 | 2.18 | 0.71 | 4–7 |
| 8. | Ala-Ser-His-Leu-Gly-Leu-Ala-Arg-Gly | 0.90 | 1.00 | 0.97 | 0. | 2.20 | 1.92 | 2.09 | 0.73 | 280–560 |
| 9. | Arg-Gln-His-Ala-Arg-Ala-Ser-His-Leu-Gly-Leu-Ala-Arg-Gly | 1.90 | 3.00 | 0.94 | 0.96 | 2.30 | 3.09 | 2.20 | 0.71 | 240–360 |

[a]Ratio of peptide mobility to solvent front migration on silica gel thin layer plates in 15:12:10:3 (by volume) 1-butanol-water-pyridine-acetic acid.
[b]Amount of peptide per 10 ml of solution to contract fully guinea pig ileum strips with Tyrode's solution.

TABLE II

| No. | Amino Acid Sequence | Amino Acid Composition (molar ratios) | | | | Thin Layer Data[a] (R$_f$ × 100) | | | | Ileum Activity[b] (nmol) |
|---|---|---|---|---|---|---|---|---|---|---|
| | | Gly | Leu | Ala | Arg | A | B | C | D | |
| 10. | Ala-Ala-Ala-Leu-Gly-Leu-Ala-Arg | 1.03 | 2.00 | 4.04 | 1.06 | 16 | 45 | 56 | — | 6–8 |
| 11. | Ala-Ala-Leu-Gly-Leu-Ala-Arg | 1.02 | 2.00 | 3.06 | 1.08 | 16 | 45 | 60 | — | 10–14 |
| 12. | Ala-Leu-Gly-Leu-Ala-Arg | 1.03 | 2.00 | 1.99 | 1.05 | 22 | 50 | 65 | — | 5–11 |

TABLE II-continued

| No. | Amino Acid Sequence | Amino Acid Composition (molar ratios) | | | | Thin Layer Data[a] (R_f × 100) | | | | Ileum Activity[b] (nmol) |
|---|---|---|---|---|---|---|---|---|---|---|
| | | Gly | Leu | Ala | Arg | A | B | C | D | |
| 13. | Asn-Lys-Pro-Leu-Gly-Leu-Ala-Arg | 1.03 | 2.00 | 1.01 | 1.03[d] | — | 17 | 30 | — | 14–27 |
| 14. | CH$_3$CO—Leu-Gly-Leu-Ala-Arg | 1.03 | 2.00 | 1.02 | 1.03 | — | 66 | 66 | — | 36–45 |
| 15. | CH$_3$CO—His-Leu-Gly-Leu-Ala-Arg | 1.05 | 2.00 | 1.01 | 1.03[c] | 63 | 48 | 13 | — | 8–17 |
| 16. | CH$_3$CO—Ala-Leu-Gly-Leu-Ala-Arg | 0.98 | 2.00 | 1.98 | 0.91 | 42 | — | — | 18 | 19–38 |
| 17. | CH$_3$CO—Ala-Leu-Gly-Leu-Ala-Can[e] | 0.99 | 2.00 | 1.98 | | 45 | — | — | 21 | 85–170 |
| 18. | CH$_3$CO—Ala-Ala-Ala-Leu-Gly-Leu-Ala-Arg | 1.21 | 2.00 | 4.27 | 1.02 | 39 | — | — | 10 | 7–13 |

[a]Ratio of peptide mobility to solvent front migration on silica gel thin layer plates in the following solvent systems by volume: A, 4:1:1 1-butanol-acetic acid-water; B, 1:1:1:1 1-butanol-ethyl acetate-acetic acid-water; C, 5:5:1:3 ethyl acetate-pyridine-acetic acid-water; D, 16:2:1:1 1-butanol-pyridine-acetic acid-water.
[b]Amount of peptide per 10 ml of Tyrode's solution to fully contract a guinea pig ileum strip.
[c]Also: His, 0.96.
[d]Also: Asn, 1.00; Lys, 1.02; Pro, 1.01.
[e]L-Canavanine (Can) has a sidechain [CH$_2$—CH$_2$—O—NH—C(=NH)—NH$_2$] resembling that of arginine (Arg) except that an oxygen atom replaces the delta methylene group.

What is claimed is:
1. Ala-Ser-His-Leu-Gly-Leu-Ala-Arg-Gly.
2. Arg-Gln-His-Ala-Arg-Ala-Ser-His-Leu-Gly-Leu-Ala-Arg-Gly.
3. Ala-Ala-Ala-Leu-Gly-Leu-Ala-Arg.
4. Ala-Ala-Leu-Gly-Leu-Ala-Arg.
5. Ala-Leu-Gly-Leu-Ala-Arg.
6. Asn-Lys-Pro-Leu-Gly-Leu-Ala-Arg.
7. CH$_3$CO-Leu-Gly-Leu-Ala-Arg.
8. CH$_3$CO-His-Leu-Gly-Leu-Ala-Arg.
9. CH$_3$CO-Ala-Leu-Gly-Leu-Ala-Arg.
10. CH$_3$CO-Ala-Leu-Gly-Leu-Ala-Can.
11. CH$_3$CO-Ala-Ala-Ala-Leu-Gly-Leu-Ala-Arg.
12. Gly-Leu-Ala-Arg.
13. Leu-Gly-Leu-Ala-Arg.
14. His-Leu-Gly-Leu-Ala-Arg.
15. Ser-His-Leu-Gly-Leu-Ala-Arg.
16. Ala-Ser-His-Leu-Gly-Leu-Ala-Arg.
17. CH$_3$CO-Ala-Ser-His-Leu-Gly-Leu-Ala-Arg.

* * * * *

UNITED STATES PATENT AND TRADEMARK OFFICE
CERTIFICATE OF CORRECTION

PATENT NO. : 4,438,029
DATED : March 20, 1984
INVENTOR(S) : Bruce W. Erickson, et al.

It is certified that error appears in the above-identified patent and that said Letters Patent are hereby corrected as shown below:

Col. 2, line 19, "satls" should read --salts--

Col. 1, line 18, "vacular" should read --vascular--

Col. 1, line 68, "vacular" should read --vascular--

Col. 3, line 41, "vacular" should read --vascular--.

Signed and Sealed this

Second Day of April 1985

[SEAL]

Attest:

DONALD J. QUIGG

Attesting Officer  Acting Commissioner of Patents and Trademarks